United States Patent [19]

Hugues et al.

[11] Patent Number: 4,691,048

[45] Date of Patent: Sep. 1, 1987

[54] PROCESS FOR REDUCING CARBONYLATION OF ALDEHYDES, USES AS HEMIACETALESTERS, CATALYZED BY COBALT CARBONYL COMPLEXES

[75] Inventors: Francois Hugues, Nanterre; Dominique Commereuc, Meudon; Yves Chauvin, Le Pecq, all of France

[73] Assignee: Institut Francais du Petrole, Rueil-Malmaison, France

[21] Appl. No.: 732,487

[22] Filed: May 10, 1985

[30] Foreign Application Priority Data

May 11, 1984 [FR] France ................................ 84 07280

[51] Int. Cl.[4] ............................................ C07C 67/24
[52] U.S. Cl. ..................... 560/240; 260/404; 260/410; 260/410.5; 260/410.6; 560/1; 560/8; 560/112; 560/122; 560/123; 560/124; 560/125; 560/126; 560/179; 564/132; 568/420; 568/428; 568/484; 568/607; 568/622; 568/625; 568/662; 568/670

[58] Field of Search ................. 560/263, 55, 106, 105, 560/19, 1, 8, 240, 112, 179, 122–126; 568/420, 428, 484, 607, 622, 625, 662, 670, 678; 564/132; 260/410.6, 410.5, 410, 404

[56] References Cited

U.S. PATENT DOCUMENTS 4,168,391 9/1979 Shinkard et al. .................... 568/902
4,431,835 2/1984 Gauthier-Lafaye et al. ....... 560/105
4,447,648 5/1984 Wegman ............................. 568/484

*Primary Examiner*—Werren B. Lone
*Attorney, Agent, or Firm*—Millen & White

[57] ABSTRACT

The invention concerns a process for reducing carbonylation of an aldehyde wherein the aldehyde is used as hemiacetalester, the reaction being conducted in the presence of a catalyst consisting of a cobalt carbonyl complex.

The hemiacetal-ester may be formed in situ by reacting an acetal with an anhydride of acid.

The process preferentially yields alkylene-glycol monoesters, free of esterified, for a ratio $H_2/CO$ ranging from 1:1 to 3:1 and preferentially 2-alkoxy aldehydes, for a ratio $H_2/CO$ ranging from 0.1:1 to 0.5:1.

9 Claims, No Drawings

PROCESS FOR REDUCING CARBONYLATION OF ALDEHYDES, USES AS HEMIACETAL-ESTERS, CATALYZED BY COBALT CARBONYL COMPLEXES

The present invention has for object a process for reducing carbonylation of aldehydes, used as hemiacetal-esters, in order to obtain alkylene-glycol derivatives such as alkylene-glycol monoethers, alkylene-glycol monoether-esters and etherified 2-hydroxy aldehydes. The reaction is conducted in the presence of a cobalt-containing catalyst, by means of a synthesis gas containing carbon monoxide and hydrogen.

The resultant alkylene-glycol derivatives may be, at will, easily converted to alkylene-glycols by conventional methods.

BACKGROUND OF THE INVENTION

Various methods for synthesizing alkylene-glycols, particularly ethylene-glycol, have been proposed in the literature.

The Japanese patent No. JP-A-52-42809, in particular, discloses a method for synthesizing ethylene-glycol from a gas mixture containing carbon monoxide and hydrogen, in the presence of a rhodium containing catalyst. However this method requires a high pressure of about 50 megapascals (MPa) or more and, accordingly, is not very attractive and difficult to industrially develop.

Another method for synthesizing ethylene-glycol has been disclosed in U.S. Pat. No. 4,087,470.

This method comprises successive steps of first converting formaldehyde to glycolic acid by carbonylation reaction with carbon monoxide, then converting glycolic acid to glycolate by esterification and, finally, hydrogenating the latter to glycol.

This method is also difficult to industrially develop, the formaldehyde carbonylation step requiring high pressures and being performed in the presence of a highly corrosive acid catalyst such as hydrofluoric acid.

It has also been proposed to produce ethylene-glycol and ethylene-glycol ethers directly from formaldehyde by reaction with the synthesis gas in the presence of rhodium or cobalt and rhodium containing catalyst (U.S. Pat. Nos. 4,079,085, and 4,144,401) the reaction taking place in the presence of an alcohol as solvent under a pressure of about 20 MPa. The selectivity to ethylene-glycol is low and the yield of free and monoetherified ethylene-glycol is not higher than 35% with respect to formaldehyde.

Recently acetals of formaldehyde or acetaldehyde have been used as starting materials for producing, in particular, ethylene-glycol or propylene-glycol monoethers by reaction with the synthesis gas, in the presence of a catalyst containing cobalt carbonyl derivatives. These monoethers may then be hydrolyzed in acid medium to the corresponding glycols.

The reaction equation can be written:

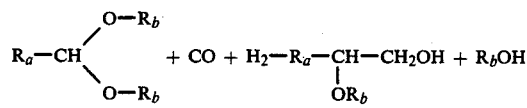

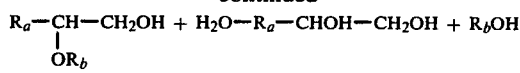

wherein $R_a$ is hydrogen or a methyl group and $R_b$ an alkyl group. The British Pat. No. GB-A-2 070 002 discloses the reducing carbonylation of formaldehyde acetals to glycol monoalkyl ethers which are then hydrolyzed to glycols.

The total yield to ethylene-glycol amounts to 76%; however the operating conditions used in the reducing carbonylation step are severe (temperature of 180°–190° C. and pressure of 20–30 MPa) and constitute a substantial disadvantage of said process.

The reducing carbonylation of acetaldehyde acetals has not been studied thoroughly and requires severe operating conditions for relatively low yields of propylene-glycol ethers, as shown in U.S. Pat. Nos. 4,356,327 and 4,390,734.

SUMMARY OF THE INVENTION

Surprisingly, it has been discovered that it was possible to obtain with good yields a mixture of alkylene-glycol monoethers, alkylene-glycol and monoether-esters and 2-alkoxy aldehydes under moderate pressure and temperature conditions, by reducing carbonylation of aldehyde hemiacetal-esters in the presence of a cobalt carbonyl complex as catalyst. The reaction is expressed:

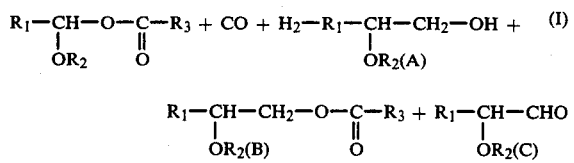

In the above formulas, each of $R_1$, $R_2$ and $R_3$ represents, independently from the others, a hydrogen atom, an alkyl group, for example from $C_1$ to $C_{12}$, an aryl group, for example from $C_6$ to $C_{14}$, an aralkyl group, for example from $C_7$ to $C_{14}$ or a cycloalkyl group, for example from $C_3$ to $C_{12}$. $R_1$, $R_2$, and $R_3$ groups may optionally carry functional groups such for example as amide, ester or ether, which do not impede the carbonylation reaction.

In the process of the invention, the hemiacetal-esters of formula I may be converted to glycol derivatives of formulas A, B and C, batchwise in an autoclave or in a plant operated in continuous manner. Compounds of formula I may be prepared in a separate preliminary step according to known methods for preparing said compounds, for example from a vinyl ether and a carboxylic acid or by reacting an acetal of formula $R_1CH(OR_2)_2$ with an anhydride of acid whose formula comprises in radical $R_3COO^-$. Compounds of formula I may also be generated in situ in the reducing carbonylation reactor, particularly by reaction of an acetal with an anhydride of acid whose formula comprises the radical $R_3COO^-$ and preferably an anhydride of carboxylic acid of formula

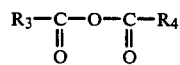

wherein $R_4$, identical to or different from $R_3$, has the same meaning as that given above for $R_3$.

The preferred starting compounds of formula I are those wherein group $R_1$ is a hydrogen atom or a methyl group; $R_2$ is a $C_1$-$C_4$ alkyl group: methyl, ethyl, propyl, isopropyl, n-butyl, secondary or tert-butyl; $R_3$ is a $C_1$-$C_4$ alkyl group and more preferably a methyl group.

When the compound of formula I is formed in situ from an acetal of formula $R_1CH(OR_2)_2$ or from an anhydride of formula

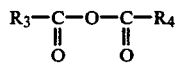

$R_1$ and RHD 2 are the above-mentioned preferred groups and the anhydride is preferably such that $R_4$ is identical to $R_3$ and consists of an alkyl group and more preferably a methyl group.

The compounds according to the above formulas A, B and C, are the three main products of the reducing carbonylation reaction of substrates of formula I in the above considered conditions.

As shown hereinafter, and in the examples, depending on the operating conditions, and particularly in relation with the $CO/H_2$ ratio, the compound C may be formed in a more or less substantial proportion with respect to compounds A and B.

In a conventional manner, compound B may be easily converted to compound A by hydrolysis. It is also easy to hydrogenate the aldehyde of formula C to a compound of formula A by known methods. The hydrolizing and hydrogenating reactions may be performed on the mixture obtained by reducing carbonylation without separation of the compounds or on compounds previously separated, for example by distillation.

When it is desired to obtain an alkylene-glycol, the produced alkylene-glycol monoether may be hydrolyzed by conventional methods, particularly by the method disclosed in GB-A-2 070 002.

By the process according to this invention it is possible to obtain, in particular, with good yields and under relatively mild conditions, free or esterified ethyleneglycol or propylene-glycol monoethers and/or 2-alkoxy acetaldehydes and/or 2-alkoxy propionaldehydes.

The carbonylation catalyst necessary for carrying out the process of the present invention is a cobalt carbonyl complex which may be introduced in the reaction medium for example as dicobalt octacarbonyl, cobalt hydride tetracarbonyl, cobalt acetate or any other cobalt compound, generally used in the so-called "oxo" reactions, giving rise in situ to a cobalt carbonyl complex in the reaction conditions. The cobalt concentration, expressed by the molar ratio cobalt/initial substrate, may be from 0.1 to 0.0001 mole/mole, preferably 0.05 to 0.001 mole/mole. Cocatalysts may optionally be used, particularly those proposed in the prior art documents for acetal carbonylation reactions.

The reducing carbonylation may be performed on substrates either pure or dissolved in an organic solvent which may consist of a saturated hydrocarbon, an aromatic hydrocarbon such as benzene or toluene, an ether, a nitrile or any other solvent not reactive in the reaction conditions and which may then be easily separated from the obtained products.

The synthesis gas used in the reaction is a mixture containing hydrogen and carbon monoxide in a molar ratio ranging from about 0.05:1 to about 10:1, preferably from about 0.1:1 to about 3:1. When the $H_2/CO$ ratio is from about 0.05:1 to about 0.5:1, 2-alkoxy aldehydes are then formed in a major proportion. When it is desired to obtain 2-alkoxy aldehydes, the synthesis gas will preferably have a $H_2/CO$ ratio from about 0.1:1 to about 0.5:1.

When the $H_2/CO$ ratio is from about 1:1 to about 10:1, free or esterified glycol monoethers are then formed in major proportion. When it is desired to form free or esterified glycol monoethers, a synthesis gas with a $H_2/CO$ ratio from about 1:1 to about 3:1 will be preferably selected.

When the synthesis gas has an intermediary ratio, for example from about 0.5:1 to about 1:1, generally a mixture of compounds A, B and C is formed.

When the product of formula I is formed in situ from an acetal and an anhydride of acid, the formation of esterified glycol monoethers is favoured as compared to that of unesterified products when anhydride is used in excess.

The pressure and temperature conditions vary in relation with the initial substrate. The pressure ranges from 5 to 25 megapascals (MPa) and preferably from 7 to 18 MPa. The temperature ranges from 70° C. to 250° C. and preferably from 100° to 170° C.

When the initial substrate is formed by reacting an anydride with an acetal, the molar ratio anhydride/acetal usefully ranges from about 0.5:1 to about 20:1 and preferably from about 1:1 ;L to 4:1.

EXAMPLES

The following examples illustrate the invention without however limiting the scope thereof.

EXAMPLE 1

A stainless-steel autoclave of 300 cc useful volume, equipped with a temperature regulation device by electric heating and with a magnetic stirrer, is fed with 40 ml of benzene, 2 millimoles of dicobaltoctacarbonyl $Co_2(CO)_8$ and 0.1 mole of 1-ethoxy ethyl acetate

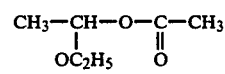

The reactor is closed and purged four times with 1 MPa of carbon monoxide-hydrogen mixture in a $CO/H_2$ ratio of 1:1. The pressure is then adjusted to 14 MPa, at room temperature, with synthesis gas having a $CO/H_2$ molar ratio of 3.5:1 and the temperature is increased to 120° C.

After 6 hours of reaction at 120° C., the autoclave is cooled down to room temperature. The observed pressure decrease, expressed in relation with the initial conditions, is 2.4 MPa. The liquid content is analyzed by vapor phase chromatography (VPC). The hemiacetalester conversion is 100%. The obtained main products and the selectivity for each of them are as follows:

| PRODUCTS | MOLAR SELECTIVITY |
|---|---|
| 2-ethoxy propionaldehyde $CH_3-CH-CHO$ $\quad\quad\ \ \|$ $\quad\quad OC_2H_5$ | 23.3% |

| PRODUCTS | MOLAR SELECTIVITY |
|---|---|
| 2-ethoxy propanol<br>$CH_3-CH-CH_2OH$<br>$\quad\quad\;\;\,|$<br>$\quad\quad\;\;\,OC_2H_5$ | 9.2% |
| 2-ethoxy propanol acetate | 2.4% |

The selectivity for a given product is equal to the percent of hemiacetal-ester or acetal converted to this product.

EXAMPLE 2

In the same apparatus and under the same operating conditions as in example 1, the reducing carbonylation of 1-ethoxy ethyl acetate is performed with a synthesis gas having a $CO/H_2$ molar ratio of 1:1, all other conditions being the same as in example 1.

The obtained liquid content is analyzed by VPC. The conversion is 100%. The obtained main products and the selectivity for each of them are as follows:

| PRODUCTS | MOLAR SELECTIVITY |
|---|---|
| 2-ethoxy propionaldehyde | 8.0% |
| 2-ethoxy propanol | 25.1% |
| 2-ethoxy propanol acetate | 6.2% |

EXAMPLE 3

0.1 mole of 1,1-diethoxy ethane, 0.11 mole of acetic anhydride and 2 m.moles of $Co_2(CO)_8$ are reacted in 40 ml of benzene in the same apparatus and conditions as in example 1. The pressure in the autoclave is brought to 14 MPa with synthesis gas having a $CO/H_2$ molar ratio of 1:1 and the temperature is set at 120° C.

After 6 hours of reaction at 120° C., the acetal conversion is 80%. The obtained main products are the same as in example 1. Analysis by VPC gives the following results:

| PRODUCTS | MOLAR SELECTIVITY |
|---|---|
| 2-ethoxy propionaldehyde | 6.5% |
| 2-ethoxy propanol | 17.5% |
| 2-ethoxy propanol acetate | 8.5% |

EXAMPLE 4

0.1 Mole of 1-methoxy methyl acetate $$CH_3O-CH_2O-C-CH_3$$
$$\quad\quad\quad\quad\quad\quad\;\;\|$$
$$\quad\quad\quad\quad\quad\quad\;\;O$$

and 1 m.mole of $Co_2(CO)_8$ are reacted in 40 ml of benzene in the same apparatus and with the same operating conditions as in example 1. The pressure in the autoclave is brought to 12 MPa with synthesis gas having a $CO/H_2$ ratio of 1:1. The temperature is set at 120° C. After 7 hours of reaction, the conversion of the hemiacetal ester is 78%. The obtained main products and the selectivity for each of them are as follows:

| PRODUCTS | MOLAR SELECTIVITY |
|---|---|
| methoxy acetaldehyde | 10% |
| 2-methoxy ethanol | 30% |
| 2-methoxy ethanol acetate | 7% |

EXAMPLE 5

0.1 mole of methylal (formaldehyde dimethylacetal $CH_2(OCH_3)_2$, 0.1 mole of acetic anhydride and 1 m.mole of $Co_2(CO)_8$ are reacted in 40 ml of benzene in the same apparatus and with the same operating conditions as in example 1. The pressure in the autoclave is brought to 12 MPa with synthesis gas having a $CO/H_2$ ratio of 1:1 and the temperature is set at 120° C. After 7 hours of reaction, the acetal conversion is 67%. The main formed products, as shown by VPC, are the following:

| PRODUCTS | MOLAR SELECTIVITY |
|---|---|
| 2-methoxy ethanol<br>$CH_3-O-CH_2-CH_2OH$ | 18.7% |
| 2-methoxy ethanol acetate<br>$CH_3O-CH_2-CH_2-O-C-CH_3$<br>$\quad\quad\quad\quad\quad\quad\quad\quad\quad\;\;\|$<br>$\quad\quad\quad\quad\quad\quad\quad\quad\quad\;\;O$ | 32.5% |

EXAMPLE 6

This example is given by way of comparison. 0.1 mole of methylal and 1 m.mole of $Co_2(CO)_8$ are reacted in 40 ml of benzene in the same apparatus and with the same operating conditions as in example 1. The pressure in the autoclave is brought to 12 MPa with synthesis gas having a $CO/H_2$ ratio of 1:1 and the temperature is set at 120° C.

After 7 hours of reaction, the acetal conversion is lower than 5%. The analysis by VPC shows the presence of carbonylation products as traces.

The comparison with example 5 shows the higher reactivity of the acetal-acetic anhydride mixture as compared with acetal alone.

What is claimed as the invention is:

1. A process for the reducing carbonylation of hemiacetal-esters comprising reacting a hemiacetalester with a gas containing hydrogen and carbon monoxide at a temperature is from 70° to 250° C. in the presence of a cobalt carbonyl complex, wherein the hemiacetalester has the formula:

$$R_1-CH-O-C-R_3$$
$$\quad\quad\;|\quad\quad\;\;\|$$
$$\quad\;\,OR_2\quad\;\,O$$

and $R_1$, $R_2$ and $R_3$ each independently are hydrogen, $C_{1-12}$-alkyl, $C_{6-14}$-aryl, $C_{7-14}$-aralkyl, or $C_{3-12}$-cycloalkyl.

2. A process according to claim 1, wherein the hemiacetalester is prepared in a step separate from the reducing carbonylation step.

3. A process according to claim 1, wherein the hemiacetalester is prepared in situ concomitantly with the carbonylation.

4. A process according to claim 1, wherein $R_1$ is hydrogen or a methyl group, $R_2$ is a $C_1$–$C_4$ alkyl group and $R_3$ is a hydrogen atom or a $C_1$–$C_4$ alkyl group.

5. A process according to claim 4, wherein $R_1$ is a hydrogen atom or a methyl group, $R_2$ is a methyl or ethyl group and $R_3$ is a methyl group.

6. A process according to claim 1, wherein the hemiacetal ester is obtained by reacting an acetal of formula $R_1$—$CH(OR_2)_2$ with an anhydride of formula

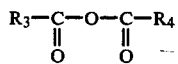

wherein $R_1$, $R_2$ and $R_3$ have the same meaning as above, $R_4$ identical to or different from $R_3$, is selected from the same groups as $R_3$, the molar ratio anhydride/acetal ranging from about 0.5:1 to about 20:1.

7. A process according to claim 6, wherein the anhydride is a symmetrical anhydride, the ratio anhydride/acetal ranging from about 1:1 to about 4:1.

8. A process according to claim 1, characterized in that, the pressure from 5 to 25 MPa, the synthesis gas composition being such that the molar ratio $H_2/CO$ is from about 1:1 to about 10:1, so as to form alkyleneglycol monoethers and esters thereof.

9. A process according to claim 1, characterized in that, the pressure from 5 to 25 MPa, the synthesis gas having such a composition that the $H_2/CO$ molar ratio is from about 0.05:1 to about 0.5:1, so as to form 2-alkoxy aldehydes.